(12) United States Patent
Miller et al.

(10) Patent No.: US 8,790,394 B2
(45) Date of Patent: Jul. 29, 2014

(54) ADJUSTABLE ARTIFICIAL CHORDEAE TENDINEAE WITH SUTURE LOOPS

(75) Inventors: Eran Miller, Moshav Beit Elazari (IL); Oz Cabiri, Macabim-Reut (IL)

(73) Assignee: Valtech Cardio, Ltd., Or Yehuda (IL)

( * ) Notice: Subject to any disclaimer, the term of this patent is extended or adjusted under 35 U.S.C. 154(b) by 692 days.

(21) Appl. No.: 12/785,717

(22) Filed: May 24, 2010

(65) Prior Publication Data

US 2011/0288635 A1 Nov. 24, 2011

(51) Int. Cl.
*A61F 2/24* (2006.01)
*A61B 17/04* (2006.01)

(52) U.S. Cl.
CPC ..... *A61B 17/0401* (2013.01); *A61B 2017/0409* (2013.01); *A61B 17/0482* (2013.01); *A61B 2017/0496* (2013.01); *A61F 2/2457* (2013.01); *A61B 2017/0414* (2013.01); *A61B 2017/0441* (2013.01)
USPC ...................................................... 623/2.1

(58) Field of Classification Search
USPC ...................................................... 623/2.1
See application file for complete search history.

(56) References Cited

U.S. PATENT DOCUMENTS

| | | |
|---|---|---|
| 4,602,911 A | 7/1986 | Ahmadi et al. |
| 4,917,698 A | 4/1990 | Carpenter et al. |
| 5,061,277 A | 10/1991 | Carpentier et al. |
| 5,104,407 A | 4/1992 | Lam et al. |
| 5,306,296 A | 4/1994 | Wright et al. |
| 5,477,856 A | 12/1995 | Lundquist |
| 5,601,572 A | 2/1997 | Middleman et al. |
| 5,669,919 A | 9/1997 | Sanders et al. |
| 5,674,279 A | 10/1997 | Wright et al. |
| 5,876,373 A | 3/1999 | Giba et al. |
| 5,961,440 A | 10/1999 | Schweich et al. |
| 5,961,539 A | 10/1999 | Northrup, III et al. |
| 6,045,497 A | 4/2000 | Schweich et al. |
| 6,050,936 A | 4/2000 | Schweich et al. |
| 6,059,715 A | 5/2000 | Schweich et al. |
| 6,165,119 A | 12/2000 | Schweich et al. |
| 6,251,092 B1 | 6/2001 | Qin et al. |
| 6,315,784 B1 | 11/2001 | Djurovic |
| 6,319,281 B1 | 11/2001 | Patel |

(Continued)

FOREIGN PATENT DOCUMENTS

| | | |
|---|---|---|
| WO | WO 01/26586 | 4/2001 |
| WO | WO 02/085251 | 10/2002 |

(Continued)

OTHER PUBLICATIONS

An Office Action dated Aug. 24, 2012, which issued during the prosecution of U.S. Appl. No. 12/563,930.

(Continued)

*Primary Examiner* — Thomas J Sweet
*Assistant Examiner* — Matthew Schall
(74) *Attorney, Agent, or Firm* — Sughrue Mion, PLLC (57) ABSTRACT

Apparatus is provided, including an artificial-chordeae-tendineae-adjustment mechanism and at least one primary artificial chordea tendinea coupled at a distal portion thereof to the artificial-chordeae-tendineae-adjustment mechanism. A degree of tension of the at least one primary artificial chordea tendinea is adjustable by the artificial-chordeae-tendineae-adjustment mechanism. One or more loops are coupled at a proximal portion of the at least one primary artificial chordea tendinea. The one or more loops are configured to facilitate suturing of the one or more loops to respective portions of a leaflet of an atrioventricular valve of a patient. Other applications are also described.

15 Claims, 7 Drawing Sheets

(56) References Cited

U.S. PATENT DOCUMENTS

| | | | |
|---|---|---|---|
| 6,332,893 B1 | 12/2001 | Mortier et al. |
| 6,406,420 B1 | 6/2002 | McCarthy et al. |
| 6,451,054 B1 | 9/2002 | Stevens |
| 6,524,338 B1 | 2/2003 | Gundry |
| 6,537,314 B2 | 3/2003 | Langberg et al. |
| 6,554,845 B1 | 4/2003 | Fleenor et al. |
| 6,564,805 B2 | 5/2003 | Garrison et al. |
| 6,569,198 B1 | 5/2003 | Wilson et al. |
| 6,589,160 B2 | 7/2003 | Schweich et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,651,671 B1 | 11/2003 | Donlon et al. |
| 6,682,558 B2 | 1/2004 | Tu et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,718,985 B2 | 4/2004 | Hlavka et al. |
| 6,723,038 B1 | 4/2004 | Schroeder et al. |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,510 B2 | 7/2004 | Vidlund et al. |
| 6,786,924 B2 | 9/2004 | Ryan et al. |
| 6,802,319 B2 | 10/2004 | Stevens et al. |
| 6,805,710 B2 | 10/2004 | Bolling et al. |
| 6,858,039 B2 | 2/2005 | McCarthy |
| 6,893,459 B1 | 5/2005 | Macoviak |
| 6,908,482 B2 | 6/2005 | McCarthy et al. |
| 6,986,775 B2 | 1/2006 | Morales et al. |
| 6,989,028 B2 | 1/2006 | Lashinski et al. |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,175,660 B2 | 2/2007 | Cartledge et al. |
| 7,186,262 B2 | 3/2007 | Saadat |
| 7,189,199 B2 | 3/2007 | McCarthy et al. |
| 7,226,467 B2 | 6/2007 | Lucatero et al. |
| 7,294,148 B2 | 11/2007 | McCarthy |
| 7,297,150 B2 | 11/2007 | Cartledge et al. |
| 7,311,728 B2 | 12/2007 | Solem et al. |
| 7,329,280 B2 | 2/2008 | Bolling et al. |
| 7,404,824 B1 | 7/2008 | Webler et al. |
| 7,431,692 B2 | 10/2008 | Zollinger et al. |
| 7,452,376 B2 | 11/2008 | Lim et al. |
| 7,455,690 B2 | 11/2008 | Cartledge et al. |
| 7,507,252 B2 | 3/2009 | Lashinski et al. |
| 7,563,267 B2 | 7/2009 | Goldfarb et al. |
| 7,563,273 B2 | 7/2009 | Goldfarb et al. |
| 7,569,062 B1 | 8/2009 | Kuehn |
| 7,588,582 B2 | 9/2009 | Starksen et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,871,433 B2 | 1/2011 | Lattouf |
| 8,142,495 B2 | 3/2012 | Hasenkam |
| 2002/0087048 A1 | 7/2002 | Brock et al. |
| 2002/0103532 A1 | 8/2002 | Langberg et al. |
| 2002/0173841 A1 | 11/2002 | Ortiz et al. |
| 2003/0050693 A1 | 3/2003 | Quijano et al. |
| 2003/0105519 A1 | 6/2003 | Fasol et al. |
| 2003/0167062 A1 | 9/2003 | Gambale et al. |
| 2003/0229350 A1 | 12/2003 | Kay |
| 2003/0233142 A1 | 12/2003 | Morales et al. |
| 2004/0024451 A1 | 2/2004 | Johnson et al. |
| 2004/0122514 A1 | 6/2004 | Fogarty et al. |
| 2004/0148021 A1 | 7/2004 | Cartledge et al. |
| 2004/0172046 A1 | 9/2004 | Hlavka et al. |
| 2004/0186566 A1 | 9/2004 | Hindrichs |
| 2004/0236419 A1 | 11/2004 | Milo |
| 2005/0004668 A1 | 1/2005 | Aklog et al. |
| 2005/0055087 A1 | 3/2005 | Starksen |
| 2005/0065601 A1 | 3/2005 | Lee et al. |
| 2005/0090827 A1 | 4/2005 | Gedebou |
| 2005/0171601 A1 | 8/2005 | Cosgrove et al. |
| 2005/0216039 A1 | 9/2005 | Lederman |
| 2005/0288781 A1 | 12/2005 | Moaddeb et al. |
| 2006/0025787 A1 | 2/2006 | Morales |
| 2006/0069429 A1 | 3/2006 | Spence et al. |
| 2006/0241656 A1 | 10/2006 | Starksen et al. |
| 2006/0241748 A1 | 10/2006 | Lee et al. |
| 2006/0287716 A1 | 12/2006 | Banbury et al. |
| 2007/0016287 A1 | 1/2007 | Cartledge et al. |
| 2007/0027536 A1 | 2/2007 | Mihaljevic et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0080188 A1 | 4/2007 | Spence et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0162111 A1 | 7/2007 | Fukamachi et al. |
| 2007/0213582 A1 | 9/2007 | Zollinger et al. |
| 2007/0219558 A1 | 9/2007 | Deutsch |
| 2007/0255397 A1 | 11/2007 | Ryan et al. |
| 2007/0255400 A1 | 11/2007 | Parravicini et al. |
| 2007/0282375 A1 | 12/2007 | Hindrichs et al. |
| 2008/0004697 A1 | 1/2008 | Lichtenstein et al. |
| 2008/0086203 A1 | 4/2008 | Roberts |
| 2008/0140116 A1 | 6/2008 | Bonutti |
| 2008/0262609 A1 | 10/2008 | Gross et al. |
| 2009/0043153 A1 | 2/2009 | Zollinger et al. |
| 2009/0088837 A1 | 4/2009 | Gillinov et al. |
| 2009/0105816 A1 | 4/2009 | Olsen et al. |
| 2009/0177266 A1 | 7/2009 | Powell et al. |
| 2009/0299409 A1 | 12/2009 | Coe et al. |
| 2010/0023117 A1 | 1/2010 | Yoganathan |
| 2010/0023118 A1 | 1/2010 | Medlock et al. |
| 2010/0042147 A1 | 2/2010 | Janovsky et al. |
| 2010/0161041 A1 | 6/2010 | Maisano et al. |
| 2010/0161043 A1 | 6/2010 | Maisano et al. |
| 2011/0011917 A1 | 1/2011 | Loulmet |

FOREIGN PATENT DOCUMENTS

| | | |
|---|---|---|
| WO | WO 02/085252 | 10/2002 |
| WO | WO 2006/097931 | 3/2006 |
| WO | WO 2006/116558 | 11/2006 |
| WO | WO 2007/136783 | 11/2007 |
| WO | WO 2008/068756 | 6/2008 |
| WO | WO 2010/073246 | 7/2010 |

OTHER PUBLICATIONS

O'Reilly S et al., "Heart valve surgery pushes the envelope," Medtech Insight 8(3): 73, 99-108 (2006).

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Swain CP et al., "An endoscopically deliverable tissue-transfixing device for securing biosensors in the gastrointestinal tract," Gastrointestinal Endoscopy 40(6): 730-734 (1994).

Odell JA et al., "Early Results of a Simplified Method of Mitral Valve Annuloplasty," Circulation 92:150-154 (1995).

An International Search Report dated Sep. 8, 2009, which issued during the prosecution of Applicant's PCT/IL09/00593.

U.S. Appl. No. 60/873,075, filed Dec. 5, 2006.

Alfieri O. et al. Novel Suture Device for Beating-Heart Mitral leaflet Approximation. Ann Thorac Surg. 2002;74: 1488-1493.

U.S. Appl. No. 60/902,146, filed Feb. 16, 2007.

(56) References Cited

OTHER PUBLICATIONS

An Office Action dated Aug. 2, 2011 which issued during the prosecution of U.S. Appl. No. 12/435,291.
U.S. Appl. No. 61/001,013, filed Oct. 29, 2007.
U.S. Appl. No. 61/132,295, filed Jun. 16, 2008.
"Two dimensional real-time ultrasonic imaging of the heart and great vessels", Mayo Clin Proc. vol. 53:271-303, 1978.
An International Search Report dated Jun. 10, 2010, which issued during the prosecution of Applicant's PCT/IL09/01209.
An Office Action dated Apr. 6, 2010, which issued during the prosecution of Applicant's U.S. Appl. No. 12/484,512.
An International Search Report and A Written Opinion, both dated Aug. 17, 2010, which issued during the prosecution of Applicant's PCT/IL10/00357.
Alfieri et al., "The edge to edge technique," The European Association for Cardio-Thoracic Surgery 14th Annual Meeting Oct. 7-11, Book of Proceed. (2000).
Alfieri et al., "An effective technique to correct anterior mitral leaflet prolapse," J Card Surg 14(6):468-470 (1999).
Alfieri et al., "The double orifice technique in mitral valve repair: a simple solution for complex problems," Journal of Thoracic Cardiovascular Surgery 122:674-681 (2001).
An International Search Report and A Written Opinion, both dated Feb. 10, 2011, which issued during the prosecution of Applicant's PCT/IL10/00890.
Alfieri, "The edge-to-edge repair of the mitral valve," [Abstract] 6th Annual NewEra Card. Care: Innovation & Technology, Heart Surg. Forum pp. 103. (2000).
Dang NC et al. "Simplified Placement of Multiple Artificial Mitral Valve Chords," The Heart Surgery Forum #2005-1005, 8 (3) (2005).
An Office Action dated Aug. 6, 2012, which issued during the prosecution of U.S. Appl. No. 12/548,991.
An Office Action dated Nov. 5, 2012, which issued during the prosecution of U.S. Appl. No. 12/795,026.
An Office Action dated Jan. 17, 2013, which issued during the prosecution of U.S. Appl. No. 12/795,192.
An Office Action dated Feb. 12, 2013, which issued during the prosecution of U.S. Appl. No. 12/926,673.
An International Search Report and a Written Opinion both dated Nov. 14, 2011, which issued during the prosecution of Applicant's PCT/IL11/00404.
An International Search Report and a Written Opinion both dated Nov. 23, 2011, which issued during the prosecution of Applicant's PCT/IL11/00446.
An International Preliminary Report on Patentability dated Nov. 27, 2012, which issued during the prosecution of Applicant's PCT/IL11/00404.
An Office Action dated Aug. 15, 2013, which issued during the prosecution of U.S. Appl. No. 12/795,192.
Dictionary.com definition of "lock", Jul. 29, 2013.
An Extended European Search Report dated Jan. 28, 2014, which issued in EP 11786226.8.
An Extended European Search Report dated Jan. 24, 2014, which issued in EP 10772090.6.
Office Action issued for U.S. Appl. No. 13/666,262 on Dec. 16.
A Notice of Allowance issued for U.S. Appl. No. 12/795,192 on Nov. 19, 2013.

ADJUSTABLE ARTIFICIAL CHORDEAE TENDINEAE WITH SUTURE LOOPS

FIELD OF THE INVENTION

The present invention relates in general to valve and chordae tendineae repair. More specifically, the present invention relates to repair of an atrioventricular valve and associated chordae tendineae of a patient.

BACKGROUND

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

Chronic or acute left ventricular dilatation can lead to papillary muscle displacement with increased leaflet tethering due to tension on chordae tendineae, as well as annular dilatation.

US Patent Application Publication 2006/0287716 to Banbury et al., describes apparatus for replacing the native chordae of a heart valve having at least two leaflets includes a prosthetic chordae assembly configured to extend from a papillary muscle to one of the at least two valve leaflets of the heart valve. The prosthetic chordae assembly has first and second end portions, and a middle portion extending therebetween. The prosthetic chordae assembly further includes a plurality of loop members interconnected at the first end portion for suturing to the papillary muscle. The middle portion is formed by two generally parallel strands of each of the loop members, and the second end portion is formed by an arcuate junction of the two strands of each of the loop members. The arcuate junctions are spaced apart and each of the junctions provides an independent location for attaching to one of the at least two valve leaflets of the heart valve.

U.S. Pat. No. 7,431,692 to Zollinger et al., which is incorporated herein by reference, describes an adjustable support pad for adjustably holding a tensioning line used to apply tension to a body organ. The adjustable support pad can include a locking mechanism for preventing slidable movement of the tensioning element in one or both directions. The locking mechanism may include spring-loaded locks, rotatable cam-like structures, and/or rotatable spool structures. The adjustable support pad may be formed from rigid, semi-rigid, and/or flexible materials, and may be formed to conform to the outer surface of a body organ. The adjustable support pad can be configured to adjustably hold one or more separate tensioning lines, and to provide for independent adjustment of one or more tensioning lines or groups thereof.

US Patent Application Publication 2007/0118151 to Davidson, which is incorporated herein by reference, describes a method and system to achieve leaflet coaptation in a cardiac valve percutaneously by creation of neochordae to prolapsing valve segments. This technique is especially useful in cases of ruptured chordae, but may be utilized in any segment of prolapsing leaflet. The technique described herein has the additional advantage of being adjustable in the beating heart. This allows tailoring of leaflet coaptation height under various loading conditions using image-guidance, such as echocardiography. This offers an additional distinct advantage over conventional open-surgery placement of artificial chordae. In traditional open surgical valve repair, chord length must be estimated in the arrested heart and may or may not be correct once the patient is weaned from cardiopulmonary bypass. The technique described below also allows for placement of multiple artificial chordae, as dictated by the patient's pathophysiology.

U.S. Pat. No. 6,626,930 to Allen et al., which is incorporated herein by reference, describes apparatus and method for the stabilization and fastening of two pieces of tissue. A single device may be used to both stabilize and fasten the two pieces of tissue, or a separate stabilizing device may be used in conjunction with a fastening device. The stabilizing device may comprise a probe with vacuum ports and/or mechanical clamps disposed at the distal end to approximate the two pieces of tissue. After the pieces of tissue are stabilized, they are fastened together using sutures or clips. One exemplary application of a suture-based fastener comprises a toggle and suture arrangement deployed by a needle, wherein the needle enters the front side of the tissue and exits the blind side. In a second exemplary application, the suture-based fastener comprises a needle connected to a suture. The needle enters the blind side of the tissue and exits the front side. The suture is then tied in a knot to secure the pieces of tissue. One example of a clip-based fastener comprises a spring-loaded clip having two arms with tapered distal ends and barbs. The probe includes a deployment mechanism which causes the clip to pierce and lockingly secure the two pieces of tissue.

U.S. Pat. No. 6,629,534 to St. Goar et al., which is incorporated herein by reference, describes methods, devices, and systems are provided for performing endovascular repair of atrioventricular and other cardiac valves in the heart. Regurgitation of an atrioventricular valve, particularly a mitral valve, can be repaired by modifying a tissue structure selected from the valve leaflets, the valve annulus, the valve chordae, and the papillary muscles. These structures may be modified by suturing, stapling, snaring, or shortening, using interventional tools which are introduced to a heart chamber. Preferably, the tissue structures will be temporarily modified prior to permanent modification. For example, opposed valve leaflets may be temporarily grasped and held into position prior to permanent attachment.

U.S. Pat. No. 6,752,813 to Goldfarb et al., which is incorporated herein by reference, describes methods and devices for grasping, and optional repositioning and fixation of the valve leaflets to treat cardiac valve regurgitation, particularly mitral valve regurgitation. Such grasping will typically be atraumatic providing a number of benefits. For example, atraumatic grasping may allow repositioning of the devices relative to the leaflets and repositioning of the leaflets themselves without damage to the leaflets. However, in some cases it may be necessary or desired to include grasping which pierces or otherwise permanently affects the leaflets. In some of these cases, the grasping step includes fixation.

US Patent Application Publication 2003/0105519 to Fasol et al., which is incorporated herein by reference, describes artificial chordae having a strand member and a first and second pair of sutures at either longitudinal end of the strand member. The artificial chordae is preferably a unitary unit, formed from inelastic flexible material. In one application, the artificial chordae comprises multiple strand members joined together at a joined end. Different sized artificial chordae are provided sized to fit the patient's heart. The appropriately sized artificial chordae is chosen by using a chordae sizing gauge having a shaft and a transverse member, to measure the space within the patient's heart where the artificial chordae is attached.

The following patents and patent application publications may be of interest:

PCT Patent Application Publication WO 07/136,783 to Cartledge et al.
U.S. Pat. No. 5,306,296 to Wright et al.
U.S. Pat. No. 6,569,198 to Wilson et al.
U.S. Pat. No. 6,619,291 to Hlavka et al.
U.S. Pat. No. 6,764,510 to Vidlund et al.
U.S. Pat. No. 7,004,176 to Lau
U.S. Pat. No. 7,101,395 to Tremulis et al.
U.S. Pat. No. 7,175,660 to Cartledge et al.
US Patent Application Publication 2003/0050693 to Quijano et al
US Patent Application Publication 2003/0167062 to Gambale et al.
US Patent Application Publication 2004/0024451 to Johnson et al.
US Patent Application Publication 2004/0148021 to Cartledge et al.
US Patent Application Publication 2004/0236419 to Milo
US Patent Application Publication 2005/0171601 to Cosgrove et al.
US Patent Application Publication 2005/0216039 to Lederman
US Patent Application Publication 2005/0288781 to Moaddeb et al.
US Patent Application Publication 2007/0016287 to Cartledge et al.
US Patent Application Publication 2007/0080188 to Spence et al.
US Patent Application Publication 2009/0177266 to Powell et al.

The following article may be of interest:

Alfieri et al., "An effective technique to correct anterior mitral leaflet prolapse," J Card Surg 14(6):468-470 (1999)
Alfieri et al., "Novel suture device for beating heart mitral leaflet approximation," Annals of Thoracic Surgery 74:1488 1493 (2002)
Alfieri et al., "The double orifice technique in mitral valve repair: a simple solution for complex problems," Journal of Thoracic Cardiovascular Surgery 122:674-681 (2001)
Alfieri et al., "The edge to edge technique," The European Association for Cardio-Thoracic Surgery 14th Annual Meeting October 7-11, Book of Proceedings. (2000)
Alfieri, "The edge-to-edge repair of the mitral valve," [Abstract] 6th Annual NewEra Cardiac Care: Innovation & Technology, Heart Surgery Forum pp. 103. (2000)
Dang N C et al. "Simplified Placement of Multiple Artificial Mitral Valve Chords," The Heart Surgery Forum #2005-1005, 8 (3) (2005)

SUMMARY OF THE INVENTION

In some applications of the present invention, apparatus is provided comprising one or more primary adjustable repair chords and one or more proximal loops coupled thereto, and an adjustment mechanism to adjust a length of the primary repair chord. The primary repair chord and the loops comprise flexible, longitudinal members (e.g., sutures or wires). The primary repair chord is coupled at a distal portion thereof to an adjustment mechanism. In some applications, the repair chord functions as artificial chordae tendineae. In other applications, the repair chord is used to adjust a distance between two portions of the ventricular wall.

In some applications of the present invention, the adjustment mechanism comprises a spool assembly which adjusts a degree of tension of the at least one primary chord. The spool assembly comprises a housing, which houses a spool to which a distal portion of the primary chord is coupled. The housing is coupled to a tissue anchor, which facilitates implantation of the spool assembly in a first portion of tissue of the heart which faces and surrounds the ventricular lumen, such as a papillary muscle or a first portion of a ventricular wall of the heart.

The second end portion (i.e., a proximal portion) of the primary chord is coupled to a proximal coupling element. The one or more loops are coupled, or otherwise fastened, to the second portion of the primary chord via the coupling element. An operating physician loops a respective suture through the one or more loops and sutures the suture to a second portion of tissue which faces and surrounds the ventricle, such as a leaflet of an atrioventricular valve (e.g., a mitral valve or a tricuspid valve) or a second portion of the ventricular wall.

Once the sutures are tied to the second portion of tissue via the loops, the spool is rotated in order to adjust a length of the primary chord. During the rotation of the spool in a first direction thereof, the longitudinal member of the primary chord is wound around the spool thereby shortening and tensioning the longitudinal member. As a result, loops coupled to the proximal portion of the primary chord, and consequently the second portion of tissue, are pulled toward the adjustment mechanism. Thus, for applications in which the primary repair chord functions as an artificial chordea tendinea, the primary chord replaces slackened native chordae tendineae and improves function of or restores normal function to the atrioventricular valve. In such an application, the adjustment mechanism is coupled to a papillary muscle or to a base of the papillary muscle, and the proximal loops are sutured to respective portions of one or more leaflets. Use of the loops distributes the adjustment force over a greater portion of the leaflet than if the primary chord would have been coupled to only one location along the leaflet.

For applications in which the repair chord is coupled to two respective portions of the ventricular wall, the two portions are drawn together, thereby restoring the dimensions of the heart wall to physiological dimensions, and drawing the leaflets toward one another.

In some applications of the present invention, the adjustment mechanism comprises a reversible locking mechanism which facilitates bidirectional rotation of the spool in order to effect both tensioning and relaxing of the primary chord. That is, the spool is wound in one direction in order to tighten the primary chord, and in an opposite direction in order to slacken the primary chord. Thus, the spool adjustment mechanism facilitates bidirectional adjustment of the primary chord.

In some applications of the present invention, the adjustable repair chord is implanted during an open-heart procedure. In these applications, the delivery tool comprises a handle and a multilumen shaft that is coupled at a distal end thereof to the adjustment mechanism. The delivery tool functions to advance the adjustment mechanism to the first portion of tissue, implant the adjustment mechanism at the first portion of tissue, and effect adjustment of the repair chord by effecting rotation of the spool. For applications in which the repair chord functions as an artificial chordea tendinea, prior to implantation of the adjustment mechanism, the distal portion of the delivery tool and the adjustment mechanism coupled thereto are advanced between the leaflets of the atrioventricular valve and into the ventricle toward the first portion of tissue. The incision made in the heart is then closed around the delivery tool and the heart resumes its normal function during the adjustment of the length of the artificial chordeae.

In some applications of the present invention, apparatus and method described herein may be used for providing artificial chordae tendineae in a left ventricle of the heart and effecting adjustment thereof. In some applications, apparatus and method described herein may be used for providing artificial chordae tendineae in a right ventricle of the heart and effecting adjustment thereof. In some applications, apparatus and method described herein may be used for providing a system to adjust a length between two portions of the heart wall.

There is therefore provided, in accordance with some applications of the present invention, apparatus, including:
 an artificial-chordeae-tendineae-adjustment mechanism;
 at least one primary artificial chordea tendinea coupled at a distal portion thereof to the artificial-chordeae-tendineae-adjustment mechanism, a degree of tension of the at least one primary artificial chordea tendinea being adjustable by the artificial-chordeae-tendineae-adjustment mechanism; and
 one or more loops coupled at a proximal portion of the at least one primary artificial chordea tendinea, the one or more loops being configured to facilitate suturing of the one or more loops to respective portions of a leaflet of an atrioventricular valve of a patient.

In some applications of the present invention, the apparatus includes one or more sutures configured to suture the one or more loops to the respective portions of the leaflet.

In some applications of the present invention, the at least one primary artificial chordea tendinea is shaped as a continuous loop.

In some applications of the present invention:
 the one or more loops includes a plurality of loops,
 the apparatus further includes a plurality of sutures, and
 each loop of the plurality of loops is configured to facilitate suturing of each suture of the plurality of sutures to a respective portion of the leaflet.

In some applications of the present invention, the distal portion of the at least one primary artificial chordea tendinea is coupled to the artificial-chordeae-tendineae-adjustment mechanism by being looped through a portion of the artificial-chordeae-tendineae-adjustment mechanism.

In some applications of the present invention, the apparatus includes a coupling element configured to couple the one or more loops to the proximal portion of the at least one primary artificial chordea tendinea.

In some applications of the present invention, the coupling element is shaped so as to define a lumen, and the proximal portion of the at least one primary artificial chordea tendinea and the one or more loops are looped through the lumen of the coupling element.

In some applications of the present invention:
 the artificial-chordeae-tendineae-adjustment mechanism includes a spool,
 the at least one primary artificial chordea tendinea is coupled to the spool;
 the spool is bidirectionally rotatable to adjust the degree of tension of the at least one primary artificial chordea tendinea.

In some applications of the present invention, the at least one primary artificial chordea tendinea is configured to be wound around spool during the rotation of the spool in a first direction thereof.

In some applications of the present invention, the apparatus includes a locking mechanism displaceable with respect to the spool so as to:
 release the spool during rotation of the spool, and
 lock in place the spool following rotation of the spool.

In some applications of the present invention, the distal portion of the at least one primary artificial chordea tendinea is looped through a portion of the spool.

In some applications of the present invention, the distal portion of the at least one primary artificial chordea tendinea is wound around a portion of the spool, and the distal portion of the at least one primary artificial chordea tendinea is configured to be unwound from around the portion of the spool following the suturing of the one or more loops to the respective portions of the leaflet.

In some applications of the present invention:
 first and second portions of the at least one primary artificial chordea tendinea extend from the artificial-chordeae-tendineae-adjustment mechanism,
 a portion between the first and second portions of the at least one primary artificial chordea tendinea defines the distal portion of the at least one primary artificial chordea tendinea,
 the first and second portions of the at least one primary artificial chordea tendinea each have free ends which define the proximal portion of the at least one primary artificial chordea tendinea,
 the one or more loops include one or more first loops and one or more second loops,
 the free end of the first portion of the at least one primary artificial chordea tendinea is coupled to the one or more first loops, and
 the free end of the second portion of the at least one primary artificial chordea tendinea is coupled to the one or more second loops.

In some applications of the present invention, the one or more first loops facilitate suturing of the one or more first loops to a first leaflet of the atrioventricular valve, and the one or more second loops facilitate suturing of the one or more second loops to the first leaflet of the atrioventricular valve.

In some applications of the present invention, the one or more first loops facilitate suturing of the one or more first loops to a first leaflet of the atrioventricular valve, and the one or more second loops facilitate suturing of the one or more second loops to a second leaflet of the atrioventricular valve.

In some applications of the present invention, the artificial-chordeae-tendineae-adjustment mechanism is configured to adjust a distance between the first and second leaflets by adjusting the first and second portions of the at least one primary artificial chordea tendinea.

There is additionally provided, in accordance with some applications of the present invention, a method including:
 coupling an artificial-chordeae-tendineae-adjustment mechanism to a first portion of cardiac tissue, the chordeae-tendineae-adjustment mechanism being coupled to a distal portion of at least one primary artificial chordea tendinea;
 extending a proximal portion of the at least one primary artificial chordea tendinea toward a leaflet of an atrioventricular valve of a patient, the proximal portion of the at least one primary artificial chordea tendinea being coupled to one or more loops;
 suturing the one or more loops to respective portions of the leaflet; and
 following the suturing, adjusting a degree of tension of the at least one primary artificial chordea tendinea using the artificial-chordeae-tendineae-adjustment mechanism.

In some applications of the present invention, adjusting the degree of tension of the at least one primary artificial chordea tendinea includes distributing a tension force on the at least one primary artificial chordea tendinea along the respective portions of the leaflet.

In some applications of the present invention, adjusting the degree of tension of the at least one primary artificial chordea tendinea includes adjusting a distance between the leaflet and the first portion of cardiac tissue.

In some applications of the present invention, adjusting the degree of tension of the at least one primary artificial chordea tendinea includes adjusting a length of the at least one primary artificial chordea tendinea between the leaflet and the first portion of cardiac tissue.

In some applications of the present invention, the at least one primary artificial chordea tendinea has first and second portions having respective free ends, the free end of the first portion being coupled to one or more first loops of the one or more loops, and the free end of the second portion being coupled to one or more second loops of the one or more loops, and the method further includes:

coupling the one or more first loops to a first leaflet of the atrioventricular valve, coupling the one or more second loops to a second leaflet of the atrioventricular valve, and adjusting a distance between the first and second leaflets by adjusting the first and second portions of the at least one primary artificial chordea tendinea with the chordeae-tendineae-adjustment mechanism.

In some applications of the present invention, the at least one primary artificial chordea tendinea has first and second portions having respective free ends, the free end of the first portion being coupled to one or more first loops of the one or more loops, and the free end of the second portion being coupled to one or more second loops of the one or more loops, and the method further includes:

coupling the one or more first loops to a first leaflet of the atrioventricular valve at a first portion thereof, and coupling the one or more second loops to the leaflet of the atrioventricular valve at a second portion thereof.

In some applications of the present invention, adjusting the degree of tension of the at least one primary artificial chordea tendinea includes adjusting the degree of tension of the at least one primary artificial chordea tendinea during a first period thereof, and the method further includes further adjusting the degree of tension of the at least one primary artificial chordea tendinea during a second period that is after the first period.

In some applications of the present invention, the artificial-chordeae-tendineae-adjustment includes a spool coupled to the distal portion of the at least one primary artificial chordea tendinea, and adjusting the degree of tension of the at least one primary artificial chordea tendinea using the artificial-chordeae-tendineae-adjustment mechanism including bidirectionally rotating the spool.

In some applications of the present invention, adjusting the degree on tension of the at least one primary artificial chordea tendinea includes unwinding a portion of the at least one primary artificial chordea tendinea before applying tension to the at least one primary artificial chordea tendinea.

In some applications of the present invention, adjusting the degree on tension of the at least one primary artificial chordea tendinea includes:

applying tension to the at least one primary artificial chordea tendinea by winding a portion of the at least one primary artificial chordea tendinea around the spool by rotating the spool in a first direction thereof, and slackening the at least one primary artificial chordea tendinea by unwinding a portion of the at least one primary artificial chordea tendinea from around the spool by rotating the spool in a second direction thereof opposite the first direction.

In some applications of the present invention, the method includes unlocking the spool prior to the adjusting the degree of tension of the at least one primary artificial chordea tendinea, and locking the spool following the adjusting the degree of tension of the at least one primary artificial chordea tendinea.

There is also provided, in accordance with some applications of the present invention, a method, including:

coupling an artificial-chordeae-tendineae-adjustment mechanism to a first portion of cardiac tissue, the chordeae-tendineae-adjustment mechanism being coupled to a distal portion of at least one artificial chordea tendinea;

extending a proximal portion of the at least one artificial chordea tendinea toward an atrioventricular valve of a patient;

suturing the proximal portion of the at least one artificial chordea tendinea to at least two leaflets of the atrioventricular valve at a middle portion of the atrioventricular valve; and following the suturing, adjusting a degree of tension of the at least one artificial chordea tendinea using the artificial-chordeae-tendineae-adjustment mechanism.

In some applications of the present invention, suturing the proximal portion of the at least one artificial chordea tendinea to the at least two leaflets of the atrioventricular valve at the middle portion of the atrioventricular valve includes creating at least two orifices in the valve for blood to pass through.

In some applications of the present invention, suturing the proximal portion of the at least one artificial chordea tendinea to the at least two leaflets of the atrioventricular valve at the middle portion of the atrioventricular valve includes creating a bridge between the leaflets.

In some applications of the present invention, suturing the proximal portion of the at least one artificial chordea tendinea to the at least two leaflets of the atrioventricular valve at the middle portion of the atrioventricular valve includes creating a plurality of sutures between the leaflets.

In some applications of the present invention, suturing the proximal portion of the at least one artificial chordea tendinea to the at least two leaflets of the atrioventricular valve includes suturing the proximal portion of the at least one artificial chordea tendinea from a ventricular surface of the valve.

In some applications of the present invention, adjusting the degree of tension of the at least one artificial chordea tendinea includes adjusting a distance between the leaflets and the first portion of cardiac tissue.

In some applications of the present invention, adjusting the degree of tension of the at least one artificial chordea tendinea includes adjusting a length of the at least one artificial chordea tendinea between the leaflets and the first portion of cardiac tissue.

The present invention will be more fully understood from the following detailed description of embodiments thereof, taken together with the drawings, in which:

DETAILED DESCRIPTION OF EMBODIMENTS

Figure 1:
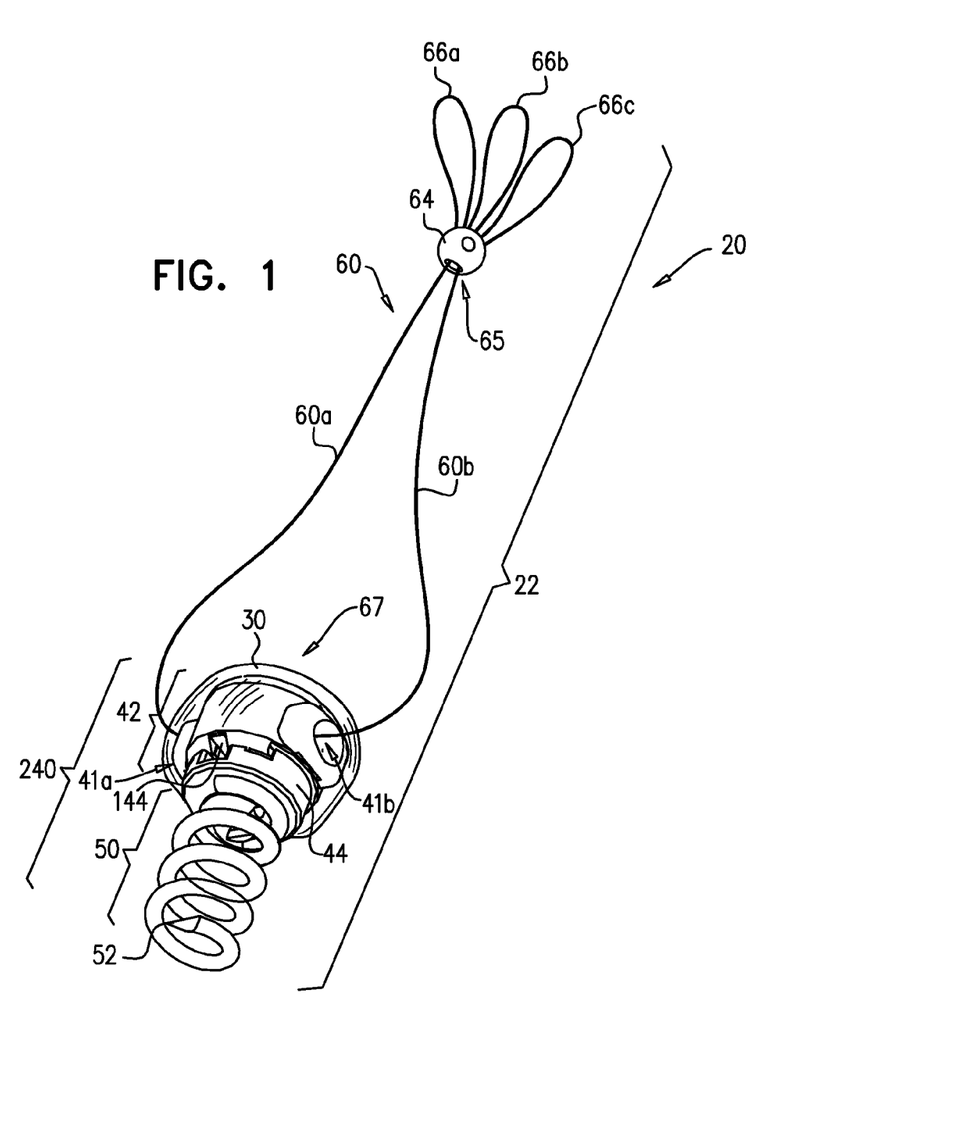
FIG. 1 is a schematic illustration of apparatus comprising a primary adjustable repair chord, a plurality of loops, and an adjustment mechanism, in accordance with some applications of the present invention.

Reference is now made to FIG. 1, which is a schematic illustration of a apparatus 20 comprising an implant 22 for adjusting a distance between first and second portions of tissue of a patient, comprising an adjustment mechanism 40, a primary repair chord 60, and one or more loops 66a, 66b, and 66c, in accordance with some applications of the present invention. Chord 60 and loops 66 comprise flexible longitudinal members (e.g., wires, sutures, or threads) which comprise a superelastic, biocompatible material (e.g., nitinol, ePTFE, PTFE, polyester, stainless steel, or cobalt chrome). Typically, repair chord 60 comprises an artificial chordea tendinea that has a proximal portion 65 and a distal portion 67. Typically, chord 60 is shaped as a continuous loop having proximal and distal portions 65 and 67. Distal portion 67 is coupled to (e.g., looped through) an adjustment mechanism 40 which comprises a housing 42. For applications in which repair chord 60 comprises an artificial chordea tendinea, adjustment mechanism 40 comprises an artificial-chordeae-tendineae-adjustment mechanism. Proximal portion 65 is coupled to a coupling element 64 (e.g., a bead, as shown, or a knot) by being looped therethrough or by being fixedly coupled thereto. Loops 66a, 66b, and 66c are looped through, fixedly attached, or otherwise coupled to coupling element 64, and thereby loops 66a, 66b, and 66c are coupled to primary chord 60. That is, for some applications of the present invention, loops 66 and proximal portion 65 of chord 60 share the same lumen of coupling element 64. As described hereinbelow, loops 66a, 66b, and 66c facilitate coupling of implant 22 to a plurality of portions of tissue of the patient. Although three loops 66 are shown, it is to be noted that any suitable number of loops 66 may be coupled to primary chord 60. The scope of the present invention includes knotting of loops 66 to proximal portion 65 of chord 60. For some applications, loops 66 are looped around a proximal looped portion of chord 60.

For example, for applications in which primary chord 60 comprises an artificial chordea tendinea, loops 66a, 66b, and 66c are coupled to a plurality of locations on a leaflet of an atrioventricular valve. Loops 66a, 66b, and 66c facilitate the passage of respective sutures therethrough which are sutured by the operating physician to the plurality of locations on the leaflet, as is described hereinbelow. The suturing of the loops to the plurality of locations distributes the adjustment force applied to the leaflet during the subsequent adjustment of primary chord 60 by adjustment mechanism 40, as described hereinbelow.

Distal portion 67 of primary chord 60 is looped through a rotatable structure (e.g., a spool, as shown hereinbelow) that is disposed within housing 42 of adjustment mechanism 40, thereby defining first and second portion 60a and 60b of chord 60. First portion 60a of primary repair chord 60 extends through a first opening 41a of housing 42, and second portion 60b of primary repair chord 60 extends through a second opening 41b in housing 42. In such an application, distal portion 67 of chord 60 defines a portion of chord 60 that is looped through the spool of adjustment mechanism 40.

Adjustment mechanism 40 comprising housing 42 and a distal cap 44, is coupled to a helical tissue anchor 50, by way of illustration and not limitation. That is, adjustment mechanism 40 may be coupled to any suitable tissue anchor known in the art. Together, adjustment mechanism 40 and tissue anchor 50 define a spool assembly 240. Helical tissue anchor 50 comprises a pointed distal tip 52 for puncturing tissue of the patient during implantation of spool assembly 240 in the first portion of tissue of the patient. Housing 42 and distal cap 44 are surrounded by a braided mesh 30 comprising biocompatible material, e.g., nitinol, polyester, ePTFE, or PTFE. Mesh 30 enhances biocompatibility and fibrosis which occurs following implantation. Additionally, during the initial implantation of assembly 240, spool housing 42 may be sutured via mesh 30 to the cardiac tissue.

Figure 2:
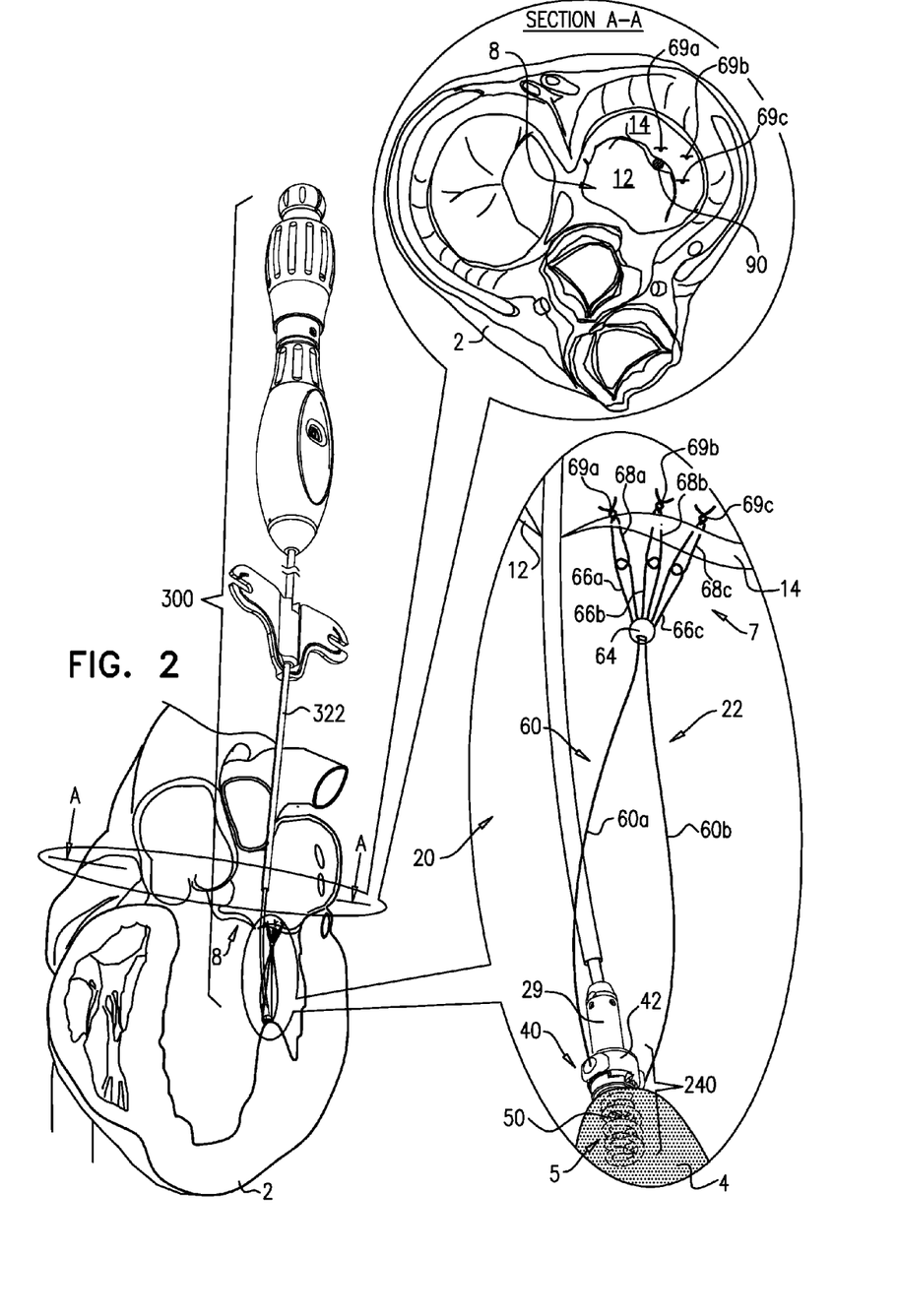
FIG. 2 is a schematic illustration of implantation of the apparatus of FIG. 1 in a heart of a patient, in accordance with some applications of the present invention.
Figure 3:
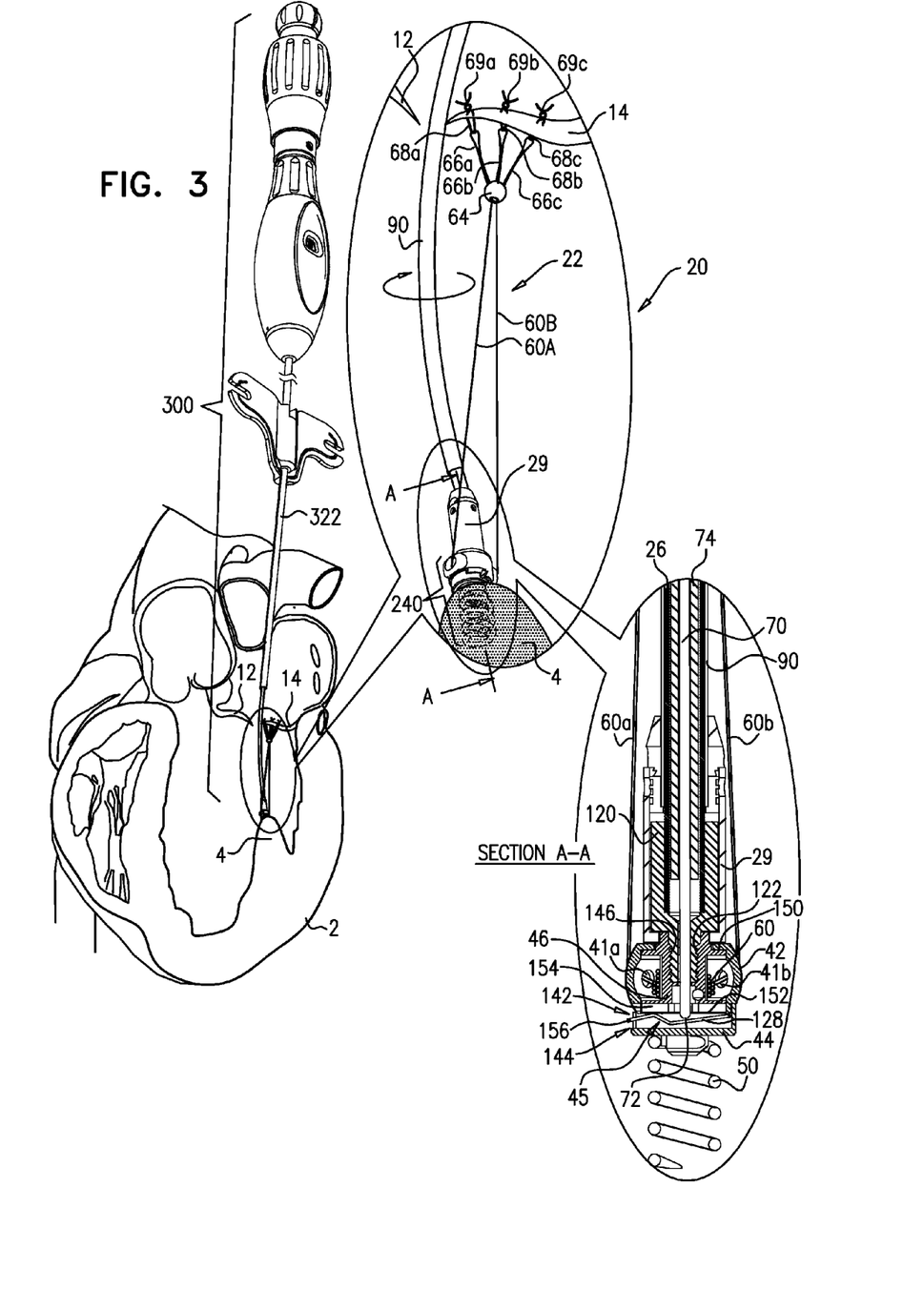
FIG. 3 is a schematic illustration of tightening the primary adjustable repair chord of FIG. 1, in accordance with some applications of the present invention.
Figure 4:
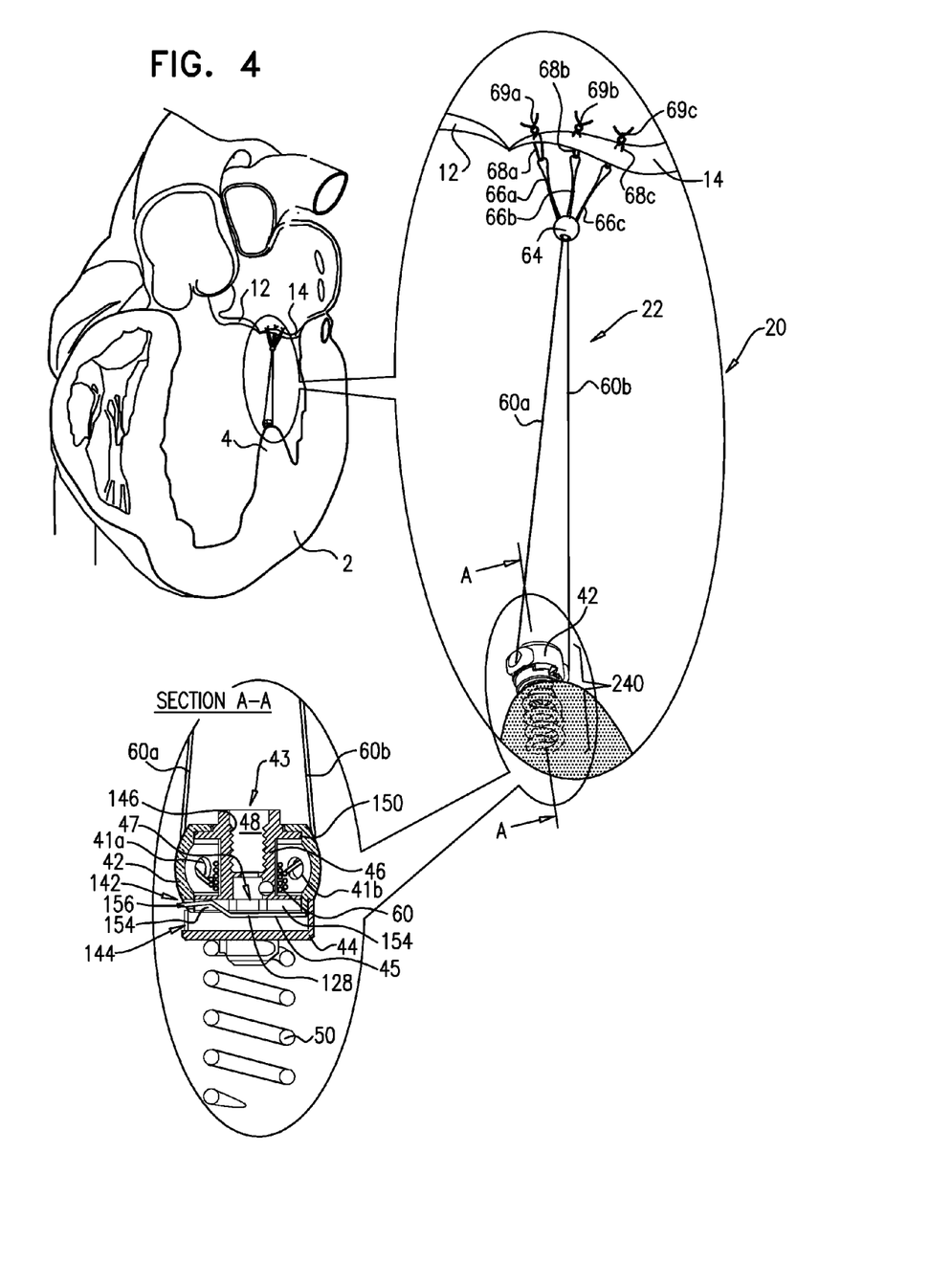
FIG. 4 is a schematic illustration of the tightened repair chord of FIG. 3, in accordance with some applications of the present invention.

Reference is now made to FIGS. 2-4 which are schematic illustrations of implantation and adjustment of apparatus 20, in accordance with some applications of the present invention. Typically, implant 22 is implanted in a heart 2 of the patient. Spool assembly 240 is implanted in a first portion of tissue 5 which faces a ventricle of heart 2, and loops 66a, 66b, and 66c are coupled to a second portion of tissue 7 which faces the ventricle of heart 2. For example, as shown, first portion 5 of tissue includes a papillary muscle 4, and second portion 7 of tissue includes a posterior leaflet 14 of a mitral valve 8 of heart 2. For some applications, first portion 5 of tissue includes the base of the papillary muscle. For other applications, first portion 5 of tissue includes a portion of the wall of heart 2, e.g., a portion of a free wall of the ventricle, a portion of the septum facing the ventricle, or a portion of the wall at the apex of the ventricle.

Typically, apparatus 20 is implanted during an open heart procedure. Implant 22 may be implanted using a delivery tool 300. For clarity of illustration, tool 300 is not shown in FIG. 2. Techniques for using tool 300 may be practiced in combination with any one of the apparatus and techniques as described in U.S. Provisional Patent Application 61/265,936 to Miller et al., entitled, "Delivery tool for implantation of spool assembly coupled to a helical anchor," filed Dec. 2, 2009, which is incorporated herein by reference.

Reference is now made to FIG. 2. First, the operating physician implants spool assembly at first portion of tissue 5, e.g., papillary muscle 4, as shown. It is to be noted that, during corkscrewing of anchor 50 into tissue 5 of the patient, the operating physician may use his or her hands to hold spool assembly 240 during corkscrewing, without using tool 300 (step not shown). Following the implanting of spool assembly 240 at papillary muscle 4, the operating physician extends primary chord 60 toward second portion of tissue 7, e.g., posterior leaflet 14, as shown. Primary chord 60 is then indirectly coupled to leaflet 14 via loops 66. The physician loops a first suture 68a through loop 66a, sutures suture 68 through a first portion of leaflet 14, and then ties suture 68a in a first knot 69a to a first location on leaflet 14. Knot 69a is typically tied at the atrial surface of leaflet 14, and then excess portions of suture 68a are clipped and removed from the body. The physician then repeats this process by suturing two other sutures 68b and 68c to leaflet 14 via loops 66b and 66c. Two other knots 69b and 69c are tied at respective locations to leaflet 14. Thus, loops 66 indirectly couple chord 60 to leaflet 14.

It is to be noted that the scope of the present invention includes the implanting of spool assembly 240 at any suitable location other than papillary muscle 4, as shown. For example, spool assembly 240 may be implanted at the base of papillary muscle 4 or at a portion of the wall of the ventricle.

FIG. 3 shows the adjusting of chord 60 by adjustment mechanism 40. Adjustment mechanism 40 is actuated by tool 300. For some applications of the present invention, tool 300 remains coupled to adjustment mechanism 40. For applications in which the physician uses his or her hands to implant spool assembly 240, tool 300 is coupled to adjustment mechanism 40 following initial implantation of spool assembly 240 and the suturing of loops 66 to leaflet 14. Alternatively, as described hereinabove, tool 300 is coupled to adjustment mechanism 40 during the advancement of spool assembly toward first portion 5 of tissue. In either application, during the subsequent adjustment of tension of primary chord 60 by adjustment mechanism 40, the incision made in heart 2 is closed around tool 300, and heart 2 resumes its normal function during the adjustment of the length of chord 60.

As shown, tension is applied to chord 60 by adjustment mechanism 40 which pulls chord 60 from a slackened state (FIG. 2) to a tensioned state (FIG. 3). This applying of tension to chord 60 adjusts a length of chord 60 between adjustment mechanism 40 and proximal portion 65 of chord 60. Additionally, this applying of tension to chord 60 adjusts a length between first and second portions 5 and 7 of tissue. As shown, adjustment mechanism 40 comprises a rotatable structure comprising a spool 46 through which distal portion 67 of chord 60 is looped. Tool 300 has an elongate multilumen shaft 322 and a proximal handle portion. That is, shaft 322 may be shaped to define only a single central lumen for passage therethrough of a torque-delivering tool 26 that is surrounded by an overtube 90. Typically, shaft 322 is sized for open-heart and/or minimally-invasive procedures and comprises a flexible material (e.g., a plastic or a plurality of strands of flexible metal such as stainless steel 304 that are bundled together) which may be bent to a desired angle. Shaft 322 is slidable along overtube 90 such that prior to tool 300 facilitating adjustment of primary chord 60 by adjustment mechanism 40, shaft 322 is slid proximally such that a distal end thereof is disposed proximally to mitral valve 8. This leaves behind overtube 90, which has a smaller diameter than shaft 322, such that the portion of tool 322 disposed between leaflets 12 and 14 has a smaller diameter which interferes less with the beating of the heart during the adjustment of primary chord 60 by adjustment mechanism 40.

A distal end portion of overtube 90 is coupled to, e.g., welded to, an adjustment mechanism holder 29 having a distal end that is reversibly coupled to a proximal portion of a housing surrounding the rotatable structure of adjustment mechanism 40. Holder 29 is shaped to define a lumen for slidable passage therethrough of a manipulator 120 which comprises a distal screwdriver head 122. Screwdriver head 122 is ultimately coupled to spool 46 and facilitates rotation of spool 46 responsively to the rotation of manipulator 120. Manipulator 120 is coupled at a proximal end thereof to a distal end of torque-delivering tool 26 which delivers torque to manipulator 120 and effects rotation of screwdriver head 122. A proximal end of torque-delivering tool 26 is coupled to a rotating mechanism at the proximal handle portion of tool 300. Shaft 322 is shaped to define a central lumen through which torque-delivering tool 26 passes.

Housing 42 of adjustment mechanism 40 defines a recessed portion 142 at a distal portion thereof. Prior to rotation of spool 46, a portion of longitudinal chord 60 is wound a few times (e.g., 3 times) around the cylindrical body portion of spool 46. Prior to rotation of spool 46, portions 60a and 60b of longitudinal chord 60 are in a slackened state (as shown in FIG. 2) and longitudinal chord 60 is wrapped a few times (e.g., 3 times) around the cylindrical portion of spool 46. FIG. 3 shows spool 46 following rotation thereof. As shown in the enlarged cross-sectional image, longitudinal chord 60 is further wound around spool 46 a few more times (e.g., an additional 5 times, as shown) around the cylindrical body portion of spool 46. Following the rotation of spool 46, portions 60a and 60b of longitudinal chord 60 are pulled taut.

In the resting state (i.e., prior to the rotation of spool 46 in order to adjust primary chord 60, following coupling of chord 60 to leaflet 14 via loops 66) chord 60 is wrapped around spool 46 a few times (e.g., three times, by way of illustration and not limitation). This winding provides excess slack to chord 60 (in case portions 60a and 60b are coupled too tightly to leaflet 14). If the physician wishes to provide slack to chord 60 or to any one of portion 60a or 60b, the physician unwinds (e.g., by unwinding chord 60 a few times from around spool 46, or by unwinding chord 60 entirely from around spool 46 so that chord 60 slides freely through spool 46 within a channel provided therein) a bit of the wrapped portion of chord 60 from around spool 46. In order to accomplish such unwinding, the physician rotates spool 46 in a direction in which it unwinds the wrapped portion of chord 60. Since chord 60 is looped through spool 46 in the channel provided therein, when chord 60 is unwound from spool 46, the physician can pull on one or both portions 60a and 60b so as to adjust, make even, or further slacken any one of or both portions 60a and 60b that extend from spool 46.

When the physician desires to pull tight chord 60, he or she effects rotation of spool 46 in a first direction, i.e., the direction opposite the second direction in which spool 46 is rotated during the unwinding of chord 60 from spool 46. Rotation of spool 46 in the first direction winds chord 60 around spool 46, while rotation of spool 46 in a second direction opposite the first direction, unwinds the portion of longitudinal chord 60 from around spool 46.

Spool 46 defines an upper surface 150, a lower surface 152 and a cylindrical body portion disposed vertically between surfaces 150 and 152. Spool 46 is shaped to provide a driving interface, e.g., a channel, which extends from an opening 43 provided by upper surface 150 to an opening 47 provided by lower surface 152 (shown in FIG. 4). A proximal portion of the driving interface is shaped to define a threaded portion 146 which may or may not be tapered. Threaded portion 146 of spool 46 is engageable by a threaded portion of screwdriver head 122. Rotation of screwdriver head 122 rotates spool 46 as the respective threaded portions of spool 46 and screwdriver head 122 engage. The cylindrical body portion of spool 46 is shaped to define one or more holes which function as respective coupling sites for coupling (e.g., looping through the one or more holes, or welding to spool 46 in the vicinity of the one or more holes) of any number of chords 60 to spool 46.

Lower surface 152 of spool 46 is shaped to define one or more (e.g., a plurality, as shown) recesses 154 which define structural barrier portions 155 of lower surface 152. It is to be noted that any suitable number of recesses 154 may be provided, e.g., between 1 and 10 recesses, circumferentially with respect to lower surface 152 of spool 46.

As shown in FIGS. 3 and 4, a locking mechanism 45 is disposed in communication with lower surface 152 of spool 46 and disposed in communication with at least in part to a lower surface of housing 42. Typically, a cap 44 maintains locking mechanism 45 in place with respect to lower surface 152 of spool 46 and lower surface of housing 42. For some applications, locking mechanism 45 is coupled, e.g., welded, to the lower surface of housing 42. Typically, locking mechanism 45 defines a mechanical element having a planar surface that defines slits. It is to be noted that the surface of locking mechanism 45 may also be curved, and not planar. Locking mechanism 45 is shaped to provide a protrusion 156 which projects out of a plane defined by the planar surface of the mechanical element. The slits of mechanism 45 define a depressible portion 128 that is disposed in communication with and extends toward protrusion 156. Depressible portion 128 is moveable in response to a force applied thereto typically by an elongate locking mechanism release rod 70 which slides through a lumen of torque-delivering tool 26. Techniques for using tool 300 and locking mechanism 45 may be practiced in combination with any one of the apparatus and techniques as described in U.S. Provisional Patent Application 61/265,936 to Miller et al., entitled, "Delivery tool for implantation of spool assembly coupled to a helical anchor," filed Dec. 2, 2009, which is incorporated herein by reference.

It is to be noted that the planar, mechanical element of locking mechanism 45 is shown by way of illustration and not limitation and that any suitable mechanical element having or lacking a planar surface but shaped to define at least one protrusion may be used together with locking mechanism 45.

Cap 44 is provided that is shaped to define a planar surface and an annular wall having an upper surface thereof. The upper surface of the annular wall is coupled to, e.g., welded to, a lower surface provided by housing 42. The annular wall of cap 44 is shaped to define a recessed portion 144 of cap 44 that is in alignment with recessed portion 142 of spool housing 42.

As shown in FIG. 3, a distal end 72 of locking mechanism release rod 70 pushes distally on depressible portion 128 in order to unlock locking mechanism 45 from spool 46. Pushing depressible portion 128 by locking mechanism release rod 70 pushes distally protrusion 156 within recessed portion 142 of housing 42 and within recessed portion 144 of cap 44, which frees protrusion 156 from recesses 154 of spool 46. Once protrusion 156 is released from recesses 154 of spool 46, the physician is able to rotate spool 46 bidirectionally in order to adjust a tension of chord 60.

When the physician rotates spool 46 in the first direction, as indicated by the arrow in FIG. 3, chord 60 is pulled tight and leaflet 14 is drawn toward adjustment mechanism 40 and toward anterior leaflet 12 of mitral valve 8.

FIG. 4 shows apparatus 20 following the removal of tool 300 of FIG. 3. As shown, portions 60*a* and 60*b* are pulled tight so as to resemble a native chord. The pulling tight of portions 60*a* and 60*b* applies tension to leaflet 14. Since loops 66*a*, 66*b*, and 66*c* are sutured via sutures 68*a*, 68*b*, and 68*c* to respective locations along leaflet 14, the tension applied to chord 60 is distributed to the plurality of locations on leaflet 14. Thus, loops 66 replace the need for implanting and adjusting a plurality of elongate artificial chords which would otherwise be coupled to the respective locations along leaflet 14. By providing loops 66, tension is applied over a greater portion of leaflet 14 using a single primary artificial chord 60. Following the removal of tool 300, depressible portion 128 is no longer depressed by tool 300, and protrusion 156 returns within a recess 154 of spool 46 so as to lock spool 46 in place and restriction rotation thereof in either direction.

For some applications of the present invention, a guidewire (not shown) remains coupled to housing 42 in order to facilitate further adjustment of chord 60 subsequently to the initial adjusting of chord 60 by tool 300.

Figure 5:
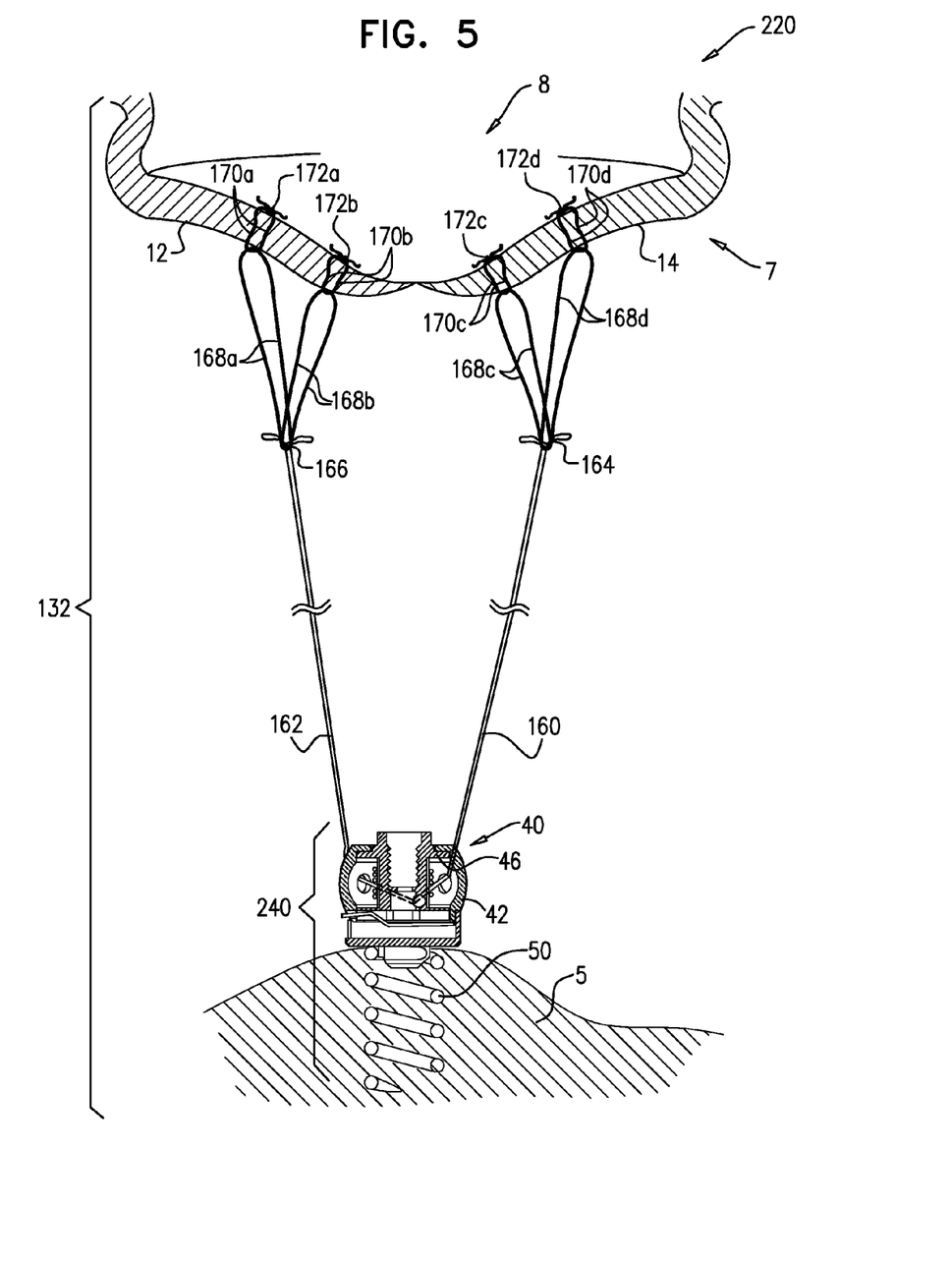
FIG. 5 is a schematic illustration of the adjustment mechanism coupled to two primary adjustable repair chords, in accordance with some applications of the present invention.

Reference is now made to FIG. 5, which is a schematic illustration of apparatus 220 comprising an implant 132 for indirectly coupling a first primary chord 160 to leaflet 14 and a second primary chord 162 to leaflet 12, in accordance with some applications of the present invention. Respective distal portions of chords 160 and 162 are coupled to spool 46 by being looped through, welded to, or otherwise coupled to spool 46. Spool assembly 240 and adjustment mechanism 40 are as described hereinabove. One or more (e.g., 2, as shown) secondary chords, or loops 168*a* and 168*b* are coupled to primary chord 162 via a first coupling 166 (e.g., a knot), and one or more (e.g., 2, as shown) secondary chords, or loops 168*c* and 168*d* are coupled to primary chord 160 via a second coupling 164 (e.g., a knot). As described hereinabove, the operating physician indirectly couples chord 162 to leaflet 12 by (a) looping respective sutures 170*a* and 170*b* through loops 168*a* and 168*b*, (b) suturing sutures 170*a* and 170*b* to leaflet 12 at respective locations, (c) creating knots 172*a* and 172*b* at the respective locations, and (d) clipping excess portions of sutures 170*a* and 170*b*. As described hereinabove, the operating physician indirectly couples chord 160 leaflet 14 by (a) looping respective sutures 170*c* and 170*d* through loops 168*c* and 168*d*, (b) suturing sutures 170*c* and 170*d* to leaflet 14 at respective locations, (c) creating knots 172*c* and 172*d* at the respective locations, and (d) clipping excess portions of sutures 170*c* and 170*d*.

Following the indirect coupling of chords 160 and 162 to leaflets 14 and 12, respectively, adjustment mechanism 40 is rotated, as described hereinabove, and chords 160 and 162 are pulled tight in order to draw leaflets 14 and 12 toward each other and to pull leaflets 14 and 12 toward adjustment mechanism 40.

The scope of the present invention includes the indirect coupling of both primary chords 160 and 162 to only one of leaflets 12 or 14, via loops 168*a-d*. The scope of the present invention includes the use of any number of primary chords coupled to adjustment mechanism 40.

It is to be noted that the scope of the present invention include the use of only one primary chord in apparatus 220. That is, for such applications, chords 160 and 162 define portions of the primary chord which extend from adjustment mechanism 40.

Figure 6A:
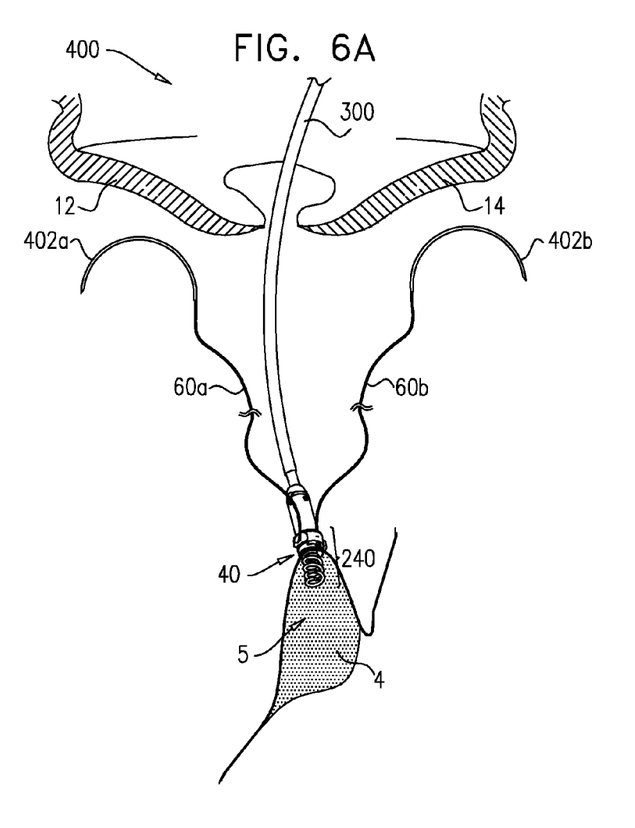
FIGS. 6A-C are schematic illustrations of the adjustment mechanism adjusting a distance between two leaflets of an atrioventricular valve, in accordance with some applications of the present invention.
Figure 6B:
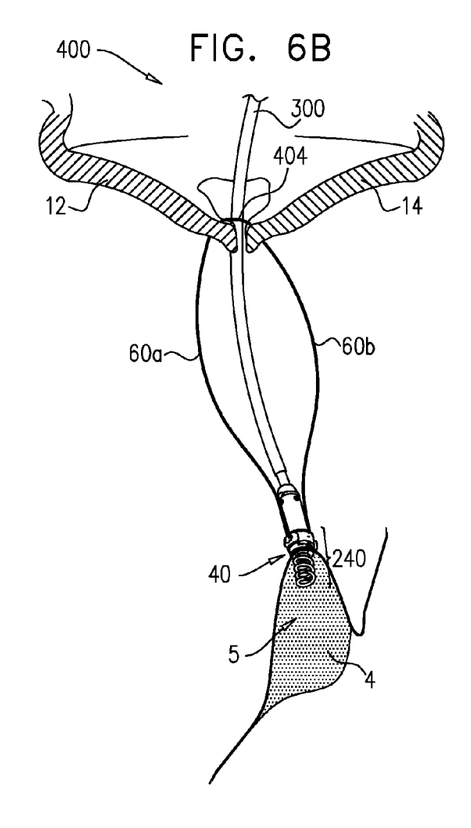
Figure 6C:
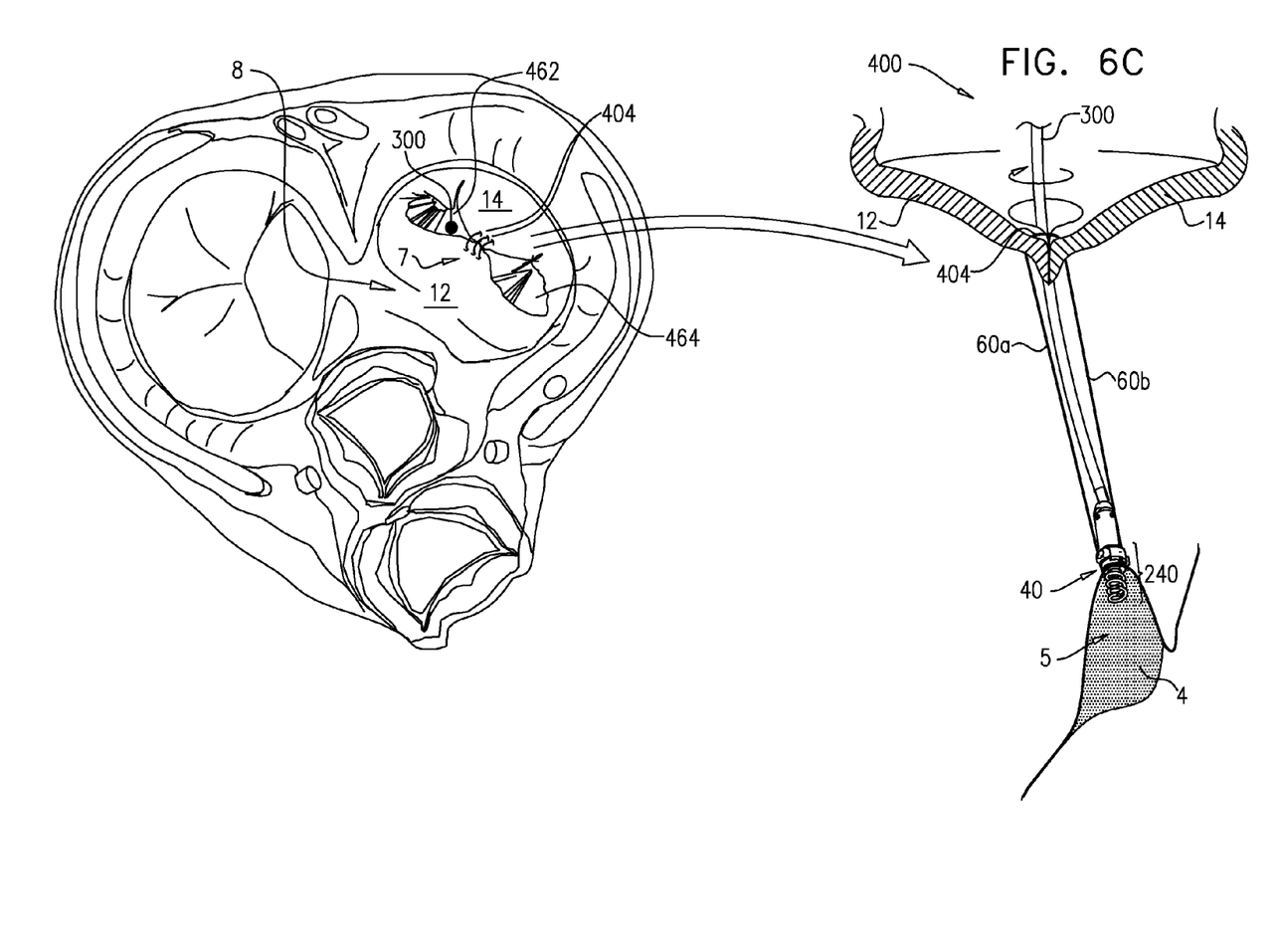

Reference is now made to FIGS. 6A-C, which are schematic illustrations of apparatus 400 comprising spool assembly 240 and portions 60*a* and 60*b* of a primary chord that are sutured to leaflets 12 and 14, in accordance with some applications of the present invention. As shown in FIG. 6A, portions 60*a* and 60*b* of the primary chord extend from adjustment mechanism 40 of spool assembly 240. The proximal free ends of each portion 60*a* and 60*b* (i.e., the proximal portion) of the primary chord are coupled to suture needles 402*a* and 402*b*, respectively. As described herein above, the primary chord is looped through adjustment mechanism 40. For other applications, portions 60*a* and 60*b* comprise independent portions which are coupled to (e.g., fixedly coupled to) a portion of adjustment mechanism 40.

In FIG. 6B, the physician sutures portions 60*a* and 60*b* to leaflets 12 and 14 from ventricular surfaces of leaflets 12 and 14. That is, needle 402*a* punctures leaflet 12 from a ventricular surface thereof in order to pass a proximal portion of portion 60*a* through leaflet 12, and needle 402*b* punctures leaflet 14 from a ventricular surface thereof in order to pass a proximal portion of portion 60*b* through leaflet 14. Portions 60*a* and 60*b* are then sutured a few times through both leaflets 12 and 14 to create a plurality of stitches 404, or a bridge between leaflets 12 and 14, e.g., as an Alfieri stitch, or edge-to-edge repair.

In FIG. 6C, portions 60*a* and 60*b* of primary chord 60 are then adjusted as described hereinabove. The adjusting pulls further together the middle portion of mitral valve 8, as shown in Section A-A. The firm coupling of leaflets 12 and 14 prevents prolapsing of leaflets 12 and 14, facilitates coaptation of leaflets 12 and 14, and creates orifices 462 and 464 in mitral valve 8 so as to facilitate blood flow from the atrium to the ventricle. Additionally, the adjusting of portions 60*a* and 60b of the primary chord draws downward leaflets 12 and 14 and adjusts the primary chord such that it functions as an artificial chordea tendinea.

Reference is now made to FIGS. 6A-C. It is to be noted that the scope of the present invention includes the use of only one of portions 60a and 60b. That is, only one chord extends from adjustment mechanism 40 and is sutured to both leaflets 12 and 14.

For some applications of the present invention, apparatus 20, 220, and 400 are used to treat an atrioventricular valve other than the mitral valve, i.e., the tricuspid valve. For these applications, apparatus 20, 220, and 400 described hereinabove as being placed in the left ventricle, are instead placed in the right ventricle.

Reference is now made to FIGS. 1-5 and 6A-C. It is to be noted that following implantation and adjustment of the primary chords, as described herein, the patient's incisions are closed. At a later stage following implantation, the primary chords may be further adjusted by reopening the incision and recoupling tool 300 to adjustment mechanism 40 in order to tighten or loosen chords 60, 160, or 162, or portions 60a and 60b of the primary chord.

Reference is again made to FIGS. 1-5 and 6A-C. It is to be noted that the scope of the present invention includes the coupling of any number of primary chords 60 to adjustment mechanism 40.

For some applications, techniques described herein are practiced in combination with techniques described in one or more of the references cited in the Background section of the present patent application.

Additionally, the scope of the present invention includes applications described in the following applications, which are incorporated herein by reference. In an application, techniques and apparatus described in one or more of the following applications are combined with techniques and apparatus described herein:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed on Feb. 16, 2007;

U.S. Provisional Patent Application 61/001,013 to Gross et al., entitled, "Segmented ring placement," filed Oct. 29, 2007;

PCT Patent Application PCT/IL07/001,503 to Gross et al., entitled, "Segmented ring placement," filed on Dec. 5, 2007, which published as PCT Patent Application Publication WO 2008/068756;

U.S. patent application Ser. No. 11/950,930 to Gross et al., entitled, "Segmented ring placement," filed on Dec. 5, 2007, which published as U.S. Patent Application Publication 2008/0262609;

U.S. Provisional Patent Application 61/132,295 to Gross et al., entitled, "Annuloplasty devices and methods of delivery therefor," filed on Jun. 16, 2008;

U.S. patent application Ser. No. 12/341,960 to Cabiri, entitled, "Adjustable partial annuloplasty ring and mechanism therefor," filed on Dec. 22, 2008, which published as U.S. Patent Application Publication 2010/0161047;

U.S. Provisional Patent Application 61/207,908 to Miller et al., entitled, "Actively-engageable movement-restriction mechanism for use with an annuloplasty structure," filed on Feb. 17, 2009;

U.S. patent application Ser. No. 12/435,291 to Maisano et al., entitled, "Adjustable repair chords and spool mechanism therefor," filed on May 4, 2009, which published as US Patent Application Publication 2010/0161041;

U.S. patent application Ser. No. 12/437,103 to Zipory et al., entitled, "Annuloplasty ring with intra-ring anchoring," filed on May 7, 2009, which published as US Patent Application Publication 2010/0286767;

PCT Patent Application PCT/IL2009/000593 to Gross et al., entitled, "Annuloplasty devices and methods of delivery therefor," filed on Jun. 15, 2009, which published as PCT Patent Application Publication WO 2010/004546;

U.S. patent application Ser. No. 12/548,991 to Maisano et al., entitled, "Implantation of repair chords in the heart," filed on Aug. 27, 2009, which published as US Patent Application Publication 2010/0161042;

U.S. patent application Ser. No. 12/608,316 to Miller et al., entitled, "Tissue anchor for annuloplasty ring," filed on Oct. 29, 2009, which published as US Patent Application Publication 2011/0106247;

U.S. Provisional Patent Application 61/265,936 to Miller et al., entitled, "Delivery tool for implantation of spool assembly coupled to a helical anchor," filed Dec. 2, 2009;

PCT Patent Application PCT/IL2009/001209 to Cabiri et al., entitled, "Adjustable annuloplasty devices and mechanisms therefor," filed on Dec. 22, 2009, which published as PCT Patent Application Publication WO 2010/073246;

U.S. patent application Ser. No. 12/689,635 to Zipory et al., entitled, "Over-wire rotation tool," filed on Jan. 19, 2010, which published as US Patent Application Publication 2010/0280604;

U.S. patent Ser. No. 12/689,693 to Hammer et al., entitled, "Application Deployment techniques for annuloplasty ring," filed on Jan. 19, 2010, which published as US Patent Application Publication 2010/0280605; and/or U.S. patent application Ser. No. 12/706,868 to Miller et al., entitled, "Actively-engageable movement-restriction mechanism for use with an annuloplasty structure," filed on Feb. 17, 2010, which published as US Patent Application Publication 2010/0211166.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a heart of a subject, the apparatus comprising an implant, the implant comprising:
   an implantable artificial-chordeae-tendineae-adjustment mechanism, configured to be coupled to tissue that faces a ventricle of the heart of the subject;
   at least one primary artificial chordea tendinea coupled at a distal portion thereof to the artificial-chordeae-tendineae-adjustment mechanism such that a degree of tension of the at least one primary artificial chordea tendinea is adjustable by the artificial-chordeae-tendineae-adjustment mechanism;

one or more loops coupled at a proximal portion of the at least one primary artificial chordea tendinea, the one or more loops being configured to facilitate suturing of the one or more loops to respective portions of a leaflet of an atrioventricular valve of a patient; and an anchor, configured to be coupled to tissue of the heart, and to be coupled, via the implantable artificial-chordeae-tendineae-adjustment mechanism, to the at least one primary artificial chordea tendinea, wherein:

the artificial-chordeae-tendineae-adjustment mechanism comprises a spool, the at least one primary artificial chordea tendinea is coupled to the spool, and the spool is bidirectionally rotatable to adjust the degree of tension of the at least one primary artificial chordea tendinea.

2. The apparatus according to claim 1, further comprising one or more sutures configured to suture the one or more loops to the respective portions of the leaflet.

3. The apparatus according to claim 1, wherein the at least one primary artificial chordea tendinea is shaped as a continuous loop.

4. The apparatus according to claim 1, wherein:

the one or more loops comprises a plurality of loops, the apparatus further comprises a plurality of sutures, and each loop of the plurality of loops is configured to facilitate suturing of each suture of the plurality of sutures to a respective portion of the leaflet.

5. The apparatus according to claim 1, wherein the distal portion of the at least one primary artificial chordea tendinea is coupled to the artificial-chordeae-tendineae-adjustment mechanism by being looped through a portion of the artificial-chordeae-tendineae-adjustment mechanism.

6. The apparatus according to claim 1, further comprising a coupling element configured to couple the one or more loops to the proximal portion of the at least one primary artificial chordea tendinea.

7. The apparatus according to claim 6, wherein the coupling element is shaped so as to define a lumen, and wherein the proximal portion of the at least one primary artificial chordea tendinea and the one or more loops are looped through the lumen of the coupling element.

8. The apparatus according to claim 1, wherein the at least one primary artificial chordea tendinea is configured to be wound around spool during the rotation of the spool in a first direction thereof.

9. The apparatus according to claim 1, further comprising a locking mechanism displaceable with respect to the spool so as to:

release the spool during rotation of the spool, and lock in place the spool following rotation of the spool.

10. The apparatus according to claim 1, wherein the distal portion of the at least one primary artificial chordea tendinea is looped through a portion of the spool.

11. The apparatus according to claim 10, wherein the distal portion of the at least one primary artificial chordea tendinea is wound around a portion of the spool, and wherein the distal portion of the at least one primary artificial chordea tendinea is configured to be unwound from around the portion of the spool following the suturing of the one or more loops to the respective portions of the leaflet.

12. The apparatus according to claim 1, wherein:

first and second portions of the at least one primary artificial chordea tendinea extend from the artificial-chordeae-tendineae-adjustment mechanism, a portion between the first and second portions of the at least one primary artificial chordea tendinea defines the distal portion of the at least one primary artificial chordea tendinea, the first and second portions of the at least one primary artificial chordea tendinea each have free ends which define the proximal portion of the at least one primary artificial chordea tendinea, the one or more loops comprise one or more first loops and one or more second loops, the free end of the first portion of the at least one primary artificial chordea tendinea is coupled to the one or more first loops, and the free end of the second portion of the at least one primary artificial chordea tendinea is coupled to the one or more second loops.

13. The apparatus according to claim 12, wherein the one or more first loops facilitate suturing of the one or more first loops to a first leaflet of the atrioventricular valve, and wherein the one or more second loops facilitate suturing of the one or more second loops to the first leaflet of the atrioventricular valve.

14. The apparatus according to claim 12, wherein the one or more first loops facilitate suturing of the one or more first loops to a first leaflet of the atrioventricular valve, and wherein the one or more second loops facilitate suturing of the one or more second loops to a second leaflet of the atrioventricular valve.

15. The apparatus according to claim 14 , wherein the artificial-chordeae-tendineae-adjustment mechanism is configured to adjust a distance between the first and second leaflets by adjusting the first and second portions of the at least one primary artificial chordea tendinea.

\* \* \* \* \*